(12) United States Patent
George et al.

(10) Patent No.: US 8,911,371 B2
(45) Date of Patent: Dec. 16, 2014

(54) TRANSDUCER HOLDER

(76) Inventors: Samuel George, Weybridge (GB); Abdul Raheem Haloob, Brentwood (GB)

( * ) Notice: Subject to any disclaimer, the term of this patent is extended or adjusted under 35 U.S.C. 154(b) by 1222 days.

(21) Appl. No.: 12/224,637

(22) PCT Filed: Feb. 28, 2007

(86) PCT No.: PCT/GB2007/000692
§ 371 (c)(1),
(2), (4) Date: Apr. 15, 2009

(87) PCT Pub. No.: WO2007/099309
PCT Pub. Date: Sep. 7, 2007

(65) Prior Publication Data
US 2010/0022888 A1   Jan. 28, 2010

(30) Foreign Application Priority Data

Mar. 1, 2006 (GB) .................................. 0604093.5
Aug. 3, 2006 (GB) .................................. 0615398.5
Nov. 6, 2006 (GB) .................................. 0622022.2

(51) Int. Cl.
*A61B 8/00* (2006.01)
*G10K 11/00* (2006.01)
*A61B 8/02* (2006.01)
*A61B 8/08* (2006.01)

(52) U.S. Cl.
CPC ................. *A61B 8/02* (2013.01); *A61B 8/4236* (2013.01); *G10K 11/004* (2013.01); *A61B 8/4209* (2013.01); *A61B 8/4281* (2013.01); *A61B 8/0866* (2013.01)
USPC ........... 600/437; 600/441; 600/443; 600/447; 601/2; 601/3; 601/4; 128/897

(58) Field of Classification Search
USPC ............................ 128/897–925; 600/437–472
See application file for complete search history.

(56) References Cited

U.S. PATENT DOCUMENTS

| 5,058,592 | A |   | 10/1991 | Whisler |
| 5,394,877 | A |   | 3/1995  | Orr |
| 5,598,845 | A | * | 2/1997  | Chandraratna et al. ........ 600/459 |
| 5,645,307 | A | * | 7/1997  | Wengler ........................ 294/157 |
| 6,210,336 | B1 | * | 4/2001 | Fredriksen ..................... 600/459 |

* cited by examiner

*Primary Examiner* — Mark Remaly
(74) *Attorney, Agent, or Firm* — Thomas C. Saitta; Steve Kelly (57) ABSTRACT

A transducer holder for holding a transducer in signal-receiving contact with a patient's body, the holder comprising: a base adherently attachable to the patient's skin; and a retainer attached or attachable to the base; wherein, in use, the retainer holds the transducer in signal-receiving contact with the patient's body and retains the transducer in the holder.

21 Claims, 9 Drawing Sheets

TRANSDUCER HOLDER

This invention relates to monitoring of patients during medical procedures, for example monitoring a mother and baby during labour. In particular, the invention relates to a transducer holder.

In medical practice, it is often desirable to monitor events occurring inside a patient's body. For example, it is common practice to monitor the fetal heartbeat during labour. Interpretation of the fetal heartbeat can give a skilled practitioner an indication of developing problems in time to take remedial action.

A fetus must obtain enough oxygen from the mother's blood, via the placenta and umbilical cord, at all times during labour. However, many factors can cause the oxygen supply to be disrupted. For example, the umbilical cord can become wrapped around the fetus or be compressed, or the mother's blood pressure can fall, diminishing the oxygen supply to the placenta. If the fetus cannot obtain enough oxygen, there is a high risk of damage to the brain, central nervous system and organs of the fetus. The longer the oxygen starvation goes on, the more likely it is that severe damage will occur. Eventually, the fetus will die.

A normal fetal heart rate is a good indicator that the fetus is extracting enough oxygen; conversely, abnormal variations in the heart rate can indicate that the fetus is being deprived of oxygen. By continuous monitoring of the fetal heart rate, an early indication of oxygen deprivation can be obtained which can allow immediate treatment and resolution of the problem, for example by performing an emergency Caesarian section or by assisting delivery with forceps or a vacuum extractor, before the fetus is harmed.

Continuous monitoring of the fetal heartbeat is especially important when epidural anaesthesia is administered, since the mother's blood pressure may drop during the procedure and lead to fetal distress as described above.

In the worst case, continuous monitoring provides a record of the state of the baby during labour, and such a record can be useful if problems cannot be avoided and litigation ensues.

The mother's uterine contractions can also be continuously monitored. This is usually done in conjunction with fetal heart rate monitoring because the fetal heart rate usually slows down during a contraction and speeds up again after the contraction. By simultaneously monitoring the contractions and the fetal heart rate, fluctuations in this normal pattern can be identified and can be indicative of fetal distress. In addition, contraction monitoring can be used as a guide to those helping the mother through labour, who may, for example, encourage a pattern of breathing or pushing complementary to the contractions. Also, in some cases, contraction monitoring can reveal that contractions are occurring even though the mother is unaware of them.

A known apparatus for performing fetal heart rate monitoring comprises a transducer, connected by a signal cable to a monitoring device. One or more such transducers may be held to the mother's abdomen.

Two main types of transducer are used in fetal heart rate monitoring, namely active transducers which emit ultrasound and detect a response by way of reflection, and passive transducers which do not emit ultrasound but simply detect sounds made by the fetal heart.

In an active transducer, a low-energy ultrasound beam is directed from the transducer towards the fetal heart. The ultrasound beam is reflected from the fetal heart, and the reflected beam is modified in amplitude and phase by the beating of the fetal heart. The reflected beam is detected by the transducer, which converts the reflected ultrasound beam into an output signal. The output signal is transmitted through the signal cable to the monitoring device, in which the output signal is interpreted and converted into a suitable visual or audio indication of the fetal heart rate. Fetal movement can also be detected by this kind of ultrasonic transducer.

A passive transducer is adapted to detect vibrations induced by the fetal heartbeat that are transmitted from the womb through the mother's body to her skin. The transducer produces an output signal which is transmitted through the signal cable to the monitoring device in which, again, the output signal is interpreted and converted into a suitable visual or audio indication.

Uterine contractions are typically monitored using a pressure-sensing transducer, which has a pick-up button disposed on one face. The pick-up button is held against the mother's abdomen, and communicates with a piezoelectric strain gauge within the transducer. Movements of the mother's abdomen, such as those caused by uterine contractions, are detected by the strain gauge and converted to an electrical signal which is transmitted through a signal cable to a monitoring device. The monitoring device interprets the signal and converts it into a suitable audio or visual indication of the frequency, duration and strength of the uterine contractions.

In the remainder of this specification, the invention will be described in the context of fetal heart rate monitoring. However, the invention could equally be used with a uterine contraction transducer or any transducer with a similar shape, including transducers that communicate wirelessly with the monitoring device. Indeed, the invention has benefit in patient monitoring in medical fields other than obstetrics.

Typically, a transducer for fetal heart rate monitoring is substantially disc-shaped, with a diameter of around 8 cm and a thickness of around 1 cm. One face of the disc is adapted for acoustic contact with the mother's abdomen.

In use, one face of the transducer is held in contact with the patient's skin. The transducer must be held securely to the patient's body, since good acoustic contact must be maintained between the transducer face and the patient's skin. A layer of acoustic gel may be used between the transducer face and the skin to improve the acoustic contact. Secure location of the transducer is a challenge because the patient will wish to move around, and perhaps be required to roll onto her side, during labour.

Figure 1:
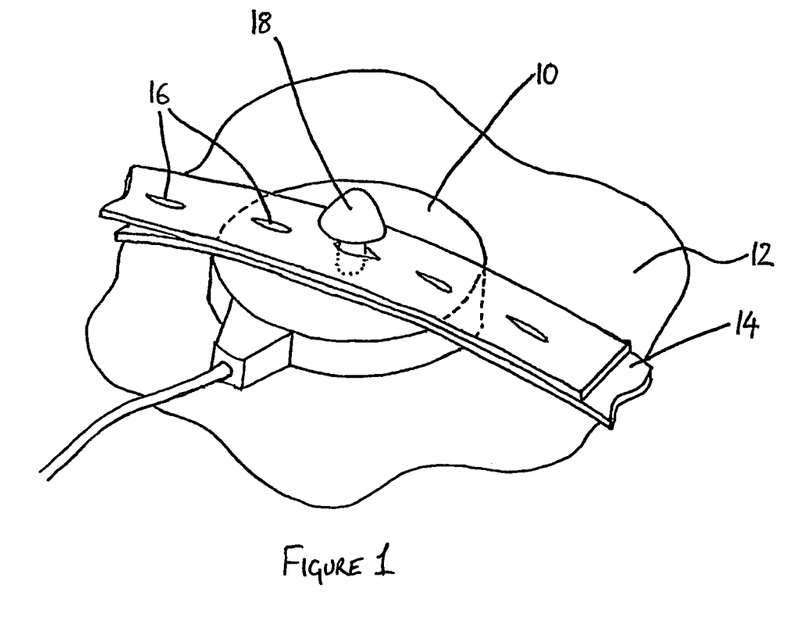

One known means for holding a transducer against a patient's skin is shown in FIG. 1 of the accompanying drawings. The transducer 10 is held against the patient's skin 12 by a strap 14 provided with a row of slits 16. The row of slits 16 extends along the length of the strap 14 along its central longitudinal axis. The strap 14 is typically made from a textile, such as cotton, and may be elastic or non-elastic. In use, the strap 14 is passed around the patient's body so that the two end regions of the strap 14 cross over one another and overlap. The strap 14 is pulled tightly to put it under tension. A stud 18, provided on the exposed face of the transducer 10 opposed to the face held against the patient, locates in two aligned slits 16, one from each end region of the strap 14. The strap 14 is thereby held in tension. The tension in the strap 14 pushes the transducer 10 against the patient's body, hence maintaining the necessary acoustic contact between the transducer 10 and the skin 12.

If more than one transducer is being used—as will be the case when fetal heart rate and the mother's contractions are being monitored simultaneously—more than one strap must also be used.

There are several disadvantages with this known transducer holding means. To provide the force required to hold the transducer on the patient's skin and maintain acoustic contact, the strap must be pulled tightly around the patient's abdomen. This can cause the patient considerable discomfort, which is particularly undesirable during a traumatic experience such as childbirth. Moreover, the or each strap hampers access to the patient's abdomen and back, hindering comforting and soothing actions such as massaging or rubbing. More seriously, straps are incompatible with the administration of epidural anaesthesia, as will now be explained.

Epidural anaesthesia is often administered for pain relief during labour, and requires the patient to roll from her back onto her side and to lie still for an extended period for administration of the anaesthetic into the spine. One or more straps around the abdomen will prevent access to the required area of the spine and must therefore be removed for the duration of the procedure. Consequently, it is common practice for the transducer to be held against the mother's abdomen by a medical practitioner while epidural anaesthesia is administered, inconveniently requiring the removal and subsequent re-fitting of the or each strap and occupying a member of medical staff to hold the transducer in position. For example, a highly-skilled midwife might typically be occupied for half an hour or more in performing this task and be unable to perform other duties. This represents a considerable waste of both human and financial resources.

The strap is so cumbersome that it can hamper the mother's mobility, which is dangerous since immobility can cause a decrease in the blood supply and, hence, the oxygen supply to the fetus, thereby increasing the risk of complications. In addition, immobility can slow down labour and increase the pain and discomfort of the mother. For these reasons, the mother is encouraged to move as much as possible.

When the mother does move, the strap can come loose or be displaced. If the strap slips, acoustic contact between the transducer and the patient may be lost, interrupting monitoring and therefore putting the fetus at risk. In addition, such a failure is inconvenient and time consuming, and can also cause further discomfort and distress to the mother.

Furthermore, and in discordance with currently preferred medical practice, transducer straps are usually re-usable. Because of the woven textile construction of the strap and the nature of childbirth, the strap tends to become soiled with blood and other bodily fluids. Even if the strap is washed and disinfected between patients, it can act as a potential source of cross-infection. Similarly, the transducers themselves must be re-used since they are costly to manufacture, and consequently also pose a risk of cross-infection between patients. Often, transducers cannot be cleaned well enough to remove all potential sources of contamination. For example, they cannot be autoclaved to kill bacteria, and in some cases they are not watertight and therefore cannot be immersed in disinfectant.

It is an aim of the present invention to provide a means for holding a transducer on a patient's skin that alleviates or overcomes the abovementioned difficulties.

Against this background, the invention resides in a transducer holder for holding a transducer in signal-receiving contact with a patient's body, the holder comprising: a base adherently attachable to the patient's skin; and a retainer attached or attachable to the base; wherein, in use, the retainer holds the transducer in signal-receiving contact with the patient's body and retains the transducer in the holder.

Throughout this specification, references to adherently attachable encompass adhesively attachable and attachable by suction.

The base may have an aperture for enabling said signal-receiving contact. The aperture may, for example, be circular. It is preferably disposed centrally with respect to the base. The aperture may be defined by a border, and the border may be ring-shaped. More than one aperture may be provided.

The aperture may be open to permit direct signal-receiving contact between the transducer and the patient's skin in use, optionally through a layer of acoustic gel. Alternatively, the aperture is closed by a barrier film through which signal-receiving contact may be effected, again optionally through one or more layers of acoustic gel. The barrier film reduces the risk of cross-infection by preventing the transducer from touching the patient's skin, in use.

If the aperture is defined by a border, the barrier film may be attached to the border. The barrier film may, for example, be attached to an upper surface of the border, facing away from the patient's skin in use. In this case, the barrier film may be dished, having a raised periphery overlying the border and a depressed centre to lie against the patient's skin in use. Alternatively, the barrier film could be attached to an undersurface of the border, facing toward the patient's skin in use.

Optionally, the base is adapted to permit said signal-receiving contact through the base, in which case the base may be uninterrupted by any apertures.

The base may, for example, be a disc. The disc may be circular or the base may have at least one enlarged anchor region. The retainer may be attached or attachable to the base at or adjacent to the or each anchor region. For example, the retainer may be attached or attachable to the base inboard of the or each anchor region. The provision of anchor regions helps to prevent peeling of the base from the patient's skin, in use.

The retainer may be integral with the base. Conveniently, the base may be flexible and the base may have self-supporting stiffness to allow easy handling of the holder. The base may comprise two or more portions, each portion being attachable to the patient's skin.

Advantageously, the base is adhesively attachable to the patient's skin. Preferably, the base has an adhesive undersurface, facing toward the patient's skin in use. The undersurface of the base may be coated with an adhesive layer. If the base has an aperture defined by a border, the adhesive layer is suitably applied to the underside of the border. Where the aperture is bridged by a barrier film, the adhesive layer may also be applied to the barrier film. In all such arrangements, a backing layer may be attached to the adhesive undersurface of the base, the backing layer being removable to expose the adhesive undersurface. This allows the holder to be conveniently packaged and handled.

The base may be attachable by suction to the patient's skin, as an alternative to the base being adhesively attachable.

Preferably, the retainer is resiliently extensible to provide location and retention forces.

At least a part of the retainer may be releasably attachable to the base. Thus, more than one part of the retainer may be releasably attachable to the base. In one arrangement, the retainer is elongate and comprises a first end and a second end, and at least one of the ends is releasably attachable to the base.

The holder may include an insertion opening through which the transducer can be introduced to and removed from the holder. The insertion opening may be defined by the retainer. For example, the retainer may be defined by one or more bands that, in use, extend over the transducer held by the holder, in which case the periphery of the insertion opening is defined by a band. Alternatively, the retainer may be defined by a membrane having free edges defining the periphery of the insertion opening. The free edges may be in the body of the membrane. For example, the free edges may be defined by a cut or slit through the membrane.

The insertion opening may alternatively be defined by the base. For example, the insertion opening may be an aperture in the base.

The insertion opening could instead be defined partially by the retainer and partially by the base. For example, the retainer could be defined by one or more bands that, in use, extend over the transducer held by the holder, in which case the periphery of the insertion opening is defined partially by a band. Alternatively, the retainer could be defined by a membrane having a free edge partially defining the periphery of the insertion opening, in which case the free edge may be at the periphery of the membrane.

The retainer may comprise one or more bands that, in use, extend over the transducer held by the holder. At least one band may be attached to the base by at least one releasable attachment. The or each band may be attached or attachable to the base at attachment points. Preferably, the base comprises at least one enlarged anchor region and the or each attachment point is located adjacent to or on the associated enlarged anchor region. For example, the or each attachment point may be located inboard of the associated enlarged anchor region.

Preferably, the or each band is substantially straight in plan view. Advantageously, the or each band has a convex cross section rising from the base from the ends of the band toward its centre. The or each band may extend over an aperture in the base.

The retainer may comprise two or more bands that, optionally, intersect. If the base is a disc, the bands may intersect at the diametric centre of the base. Preferably, the bands are attached or attachable to the base at attachment points, although it is also possible for the or each band to be integral with the base. The attachment points may be equi-angularly spaced around the base. Alternatively, the bands may be parallel to one another.

Instead of bands, the retainer may comprise a membrane that, in use, extends over the transducer held by the holder. The membrane may have a convex cross section rising from the base from the edges of the membrane toward its centre. The membrane may be attached or attachable to the base around a major portion of its periphery, a minor unattached peripheral portion of the membrane having a free edge. A free edge portion of the membrane may be releasably attachable to the base. Preferably, the membrane is part-circular and the free edge defines a chord of the circle. Alternatively, the membrane may be attached or attachable to the base around the whole of its periphery.

The invention extends to the combination of a transducer held by the transducer holder as previously described. The base of the holder may have an aperture wider than the face of the transducer that is to be in signal-receiving contact with the patient's body. Alternatively, the holder may have an aperture narrower than the face of the transducer that is to be in signal-receiving contact with the patient's body. Preferably, the retainer is extended elastically to accommodate the transducer.

The inventive concept also embraces a method for holding a transducer in signal-receiving contact with a patient's body, the method comprising: adherently attaching a transducer holder to the patient's skin; and removably attaching the transducer to the holder so that the transducer is in signal-receiving contact with the patient's body.

Also within the inventive concept is a method for holding a transducer in signal-receiving contact with a patient's body, the method comprising: removably attaching a transducer to a transducer holder; and then adherently attaching the transducer holder to the patient's skin so that the transducer is in signal-receiving contact with the patient's body.

In either of the methods described above, the holder may be adhesively attached to the skin. For example, the holder may be attached to the skin by applying an adhesive undersurface of the holder to the skin. Furthermore, either method may include removing a backing layer to expose the adhesive undersurface before the holder is attached to the skin. The methods may include applying an adhesive to the undersurface of the holder before attaching the holder to the skin. Alternatively, the holder may be attached to the patient's skin by first applying an adhesive to an area of the patient's skin, and then applying the holder to the adhesive.

The holder may be attached to the patient's skin by suction, as an alternative to adhesively attaching the holder to the skin.

In all of these methods, a layer of acoustic gel may be applied to at least one of the patient's skin, the transducer holder, and the transducer.

The methods of the invention may further comprise removing the transducer from the holder, leaving the holder attached to the patient's skin. For example, a plurality of holders may be attached to the patient's skin at different locations and, following removal of the transducer from one holder of the plurality, that transducer may be attached to another holder of the plurality.

A holder may be removed from the patient's skin and relocated to another location on the patient's skin. The transducer may be retained in the holder during said relocation.

The transducer is preferably attached to the holder by insertion through an insertion opening. In that case, the transducer may be removed from the holder through the insertion opening. Preferably, the insertion opening deforms resiliently to allow the transducer to pass during said insertion or removal, such that insertion or removal overcomes resilient resistance. The tension of means defining the insertion opening may be adjusted before said insertion or removal.

The transducer may be attached to the holder by attaching a first part of the holder to a second part of the holder. Furthermore, the first part of the holder may be detached before attaching the transducer to the holder. The transducer may be removed from the holder by detaching the first part of the holder.

The holder may comprise at least one part arranged to apply a retention force to the transducer. The retention force may be adjusted by detaching said part, applying or relaxing tension in that part, and re-attaching that part. Furthermore, the transducer holder may be attached to the patient's skin so that the at least one part arranged to apply a retention force to the transducer lies against the patient's skin before the transducer is attached to the transducer holder.

The transducer holder may be attached to the patient's skin by first attaching a first portion of the transducer holder to the skin, and then attaching a second portion of the transducer holder to the skin. The transducer may be attached to the transducer holder between the first and second portions. For example, the transducer holder may be attached to the transducer holder by attaching the first portion to the skin, placing the transducer against the skin adjacent the first portion, and attaching the second portion to the skin adjacent the transducer.

Because the transducer holder of the invention is attached to the patient only in the location where the measurement is required, the present invention affords the patient significantly less disturbance, discomfort and distress than other means for holding a transducer, for example, the strap of FIG. 1. A particular benefit is that epidural anaesthesia may be administered while a transducer remains in its holder, because access to the patient's spine is unrestricted.

In general, the transducer holder and transducer may be fitted to the patient at the beginning of the procedure and left in place throughout. Alternatively, the transducer holder may be left in place while the transducer is removed, for example if the patient is to be moved. The transducer can then be easily re-inserted into the transducer holder with the minimum of discomfort to the patient. Similarly, two or more transducer holders could be attached to the abdomen in a plurality of locations at the start of a procedure, and transducers may be fitted to the transducer holders only when required during the procedure, or one transducer could be moved around the abdomen between a plurality of pre-applied holders. Moreover, the transducer could be inserted or removed from the transducer holder before or after the transducer holder is attached to the patient's skin.

The transducer holder of the invention is particularly suitable to be manufactured from low-cost, readily available materials such as polymer sheets or films and is simple in construction. Consequently, the holder can be manufactured cheaply and is suitable for once-only, disposable use, avoiding the risks of cross-infection as well as the inconvenience and expense of cleaning and disinfecting associated with re-use of medical devices.

Reference has already been made to FIG. 1, which is a perspective drawing of a fetal heart rate transducer in use with a known strap-type transducer holding means in position on a patient. The present invention will now be described, by way of example only, with reference to the remaining drawings, in which.

Figure 2:
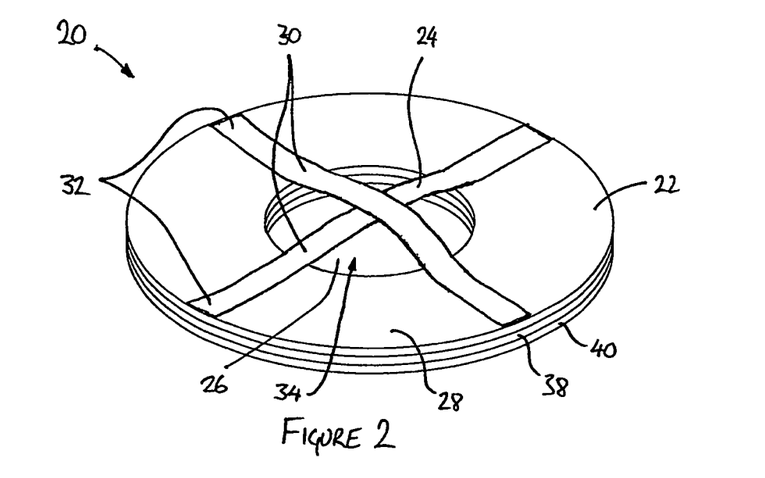
FIG. 2 is a perspective drawing of a transducer holder according to a first embodiment of the present invention.
Figure 3:
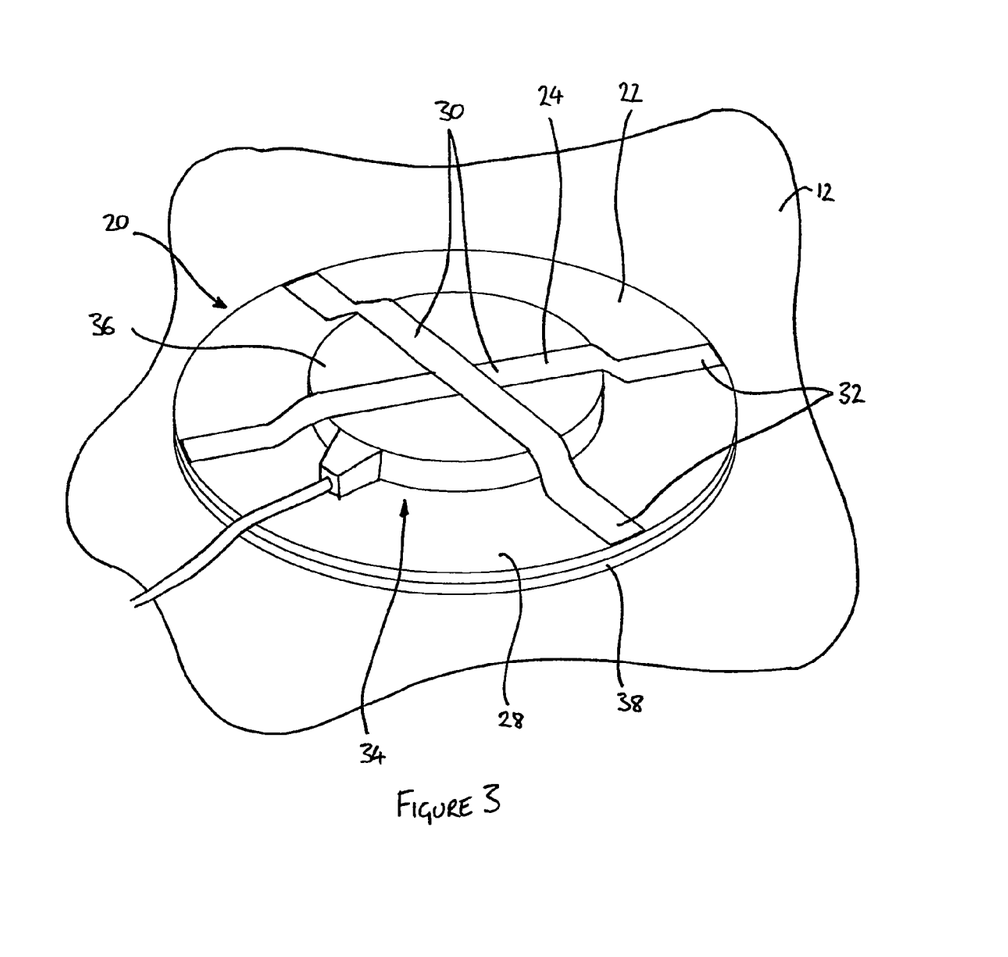
FIG. 3 is a perspective drawing of the transducer holder of FIG. 2, in use holding a transducer in a desired position on a patient's abdomen.
Figure 4:
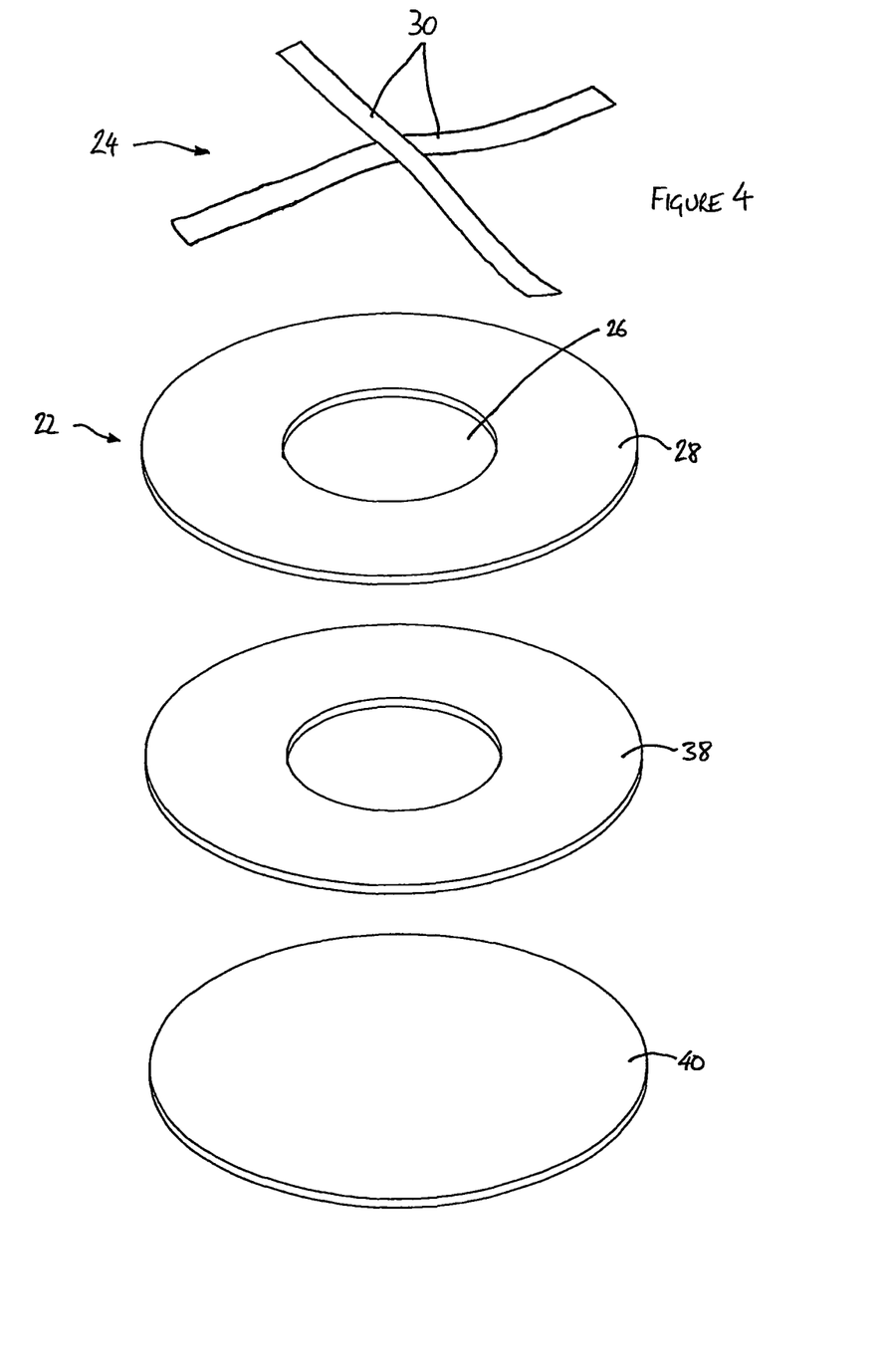
FIG. 4 is an exploded drawing of the transducer holder of FIG. 2.

Referring firstly to FIGS. 2 to 4, in a first embodiment of the present invention there is provided a transducer holder 20, comprising a base 22 and an elastic retainer 24. The base 22 is a flexible disc with a circular aperture 26 in its centre defining an annular ring 28. The aperture 26 is dimensioned to receive the face of a transducer. In use, the base 22 is adhesively attached to a patient's body, at a desired location. The elastic retainer 24 extends over the aperture 26 to hold a transducer both within the holder 20 and with respect to a patient to whom the holder 20 is attached.

Whilst the base 22 is flexible to conform to a patient's body contours, it is advantageous for the base 22 to have some self-supporting stiffness so that the holder 20 can easily be removed from packaging and applied to the patient's skin 12 without curling up, wrinkling or otherwise unhelpfully deforming.

In this embodiment, the elastic retainer 24 comprises two elastic strips or bands 30. The bands 30 are attached to the ring 28 at attachment points 32 at or close to the ends of the bands 30. The attachment points 32 are equi-angularly spaced around the aperture 26. The bands 30 therefore run diametrically across the base 22 from one side of the ring 28 over the aperture 26 to the opposite side of the ring 28 and intersect orthogonally at the diametric centre of the base 22 and the aperture 26.

The bands 30 are generally straight when viewed in plan but when viewed from the side, the bands 30 curve upwardly moving inwardly from the ring 28 to the diametric centre of the base 22. A cross-section along one of the bands 30 is a shallow hump shape. This aids insertion of a transducer as will now be described.

The ring 28, the bands 30, and particularly the gaps between adjacent attachment points 32, define insertion openings 34 through which a transducer 36 can be passed to lie under, and be restrained by, the intersecting bands 30. In that position, when the transducer 36 is centrally disposed with respect to the base 22, the transducer 36 is received within the aperture 26 where it is held in acoustic contact with the patient's body.

Each insertion opening 34 is shaped and dimensioned so that, when the transducer 36 is passed through an insertion opening 34 into the space between the bands 30 and the base 22, the bands 30 hold the transducer 36 both within the holder 20 and with respect to the patient to whom the holder 20 is attached. More specifically, the gaps between adjacent attachment points 32 and the length of the bands 30 are such that the bands 30 must deform elastically to admit the transducer 36. The transducer 36 is thereby held resiliently within the embrace of the bands 30. The holding force of the bands 30 is sufficient that the transducer 36 is held within the holder 20 under the normal conditions of use, for example when the patient moves. However, the transducer 36 can easily be removed from the holder 20 through the insertion opening 34 when required by manipulating and stretching the bands 30, or simply by pulling the transducer 36 out through the insertion opening 34 against the resilience of the bands 30.

Figure 5:
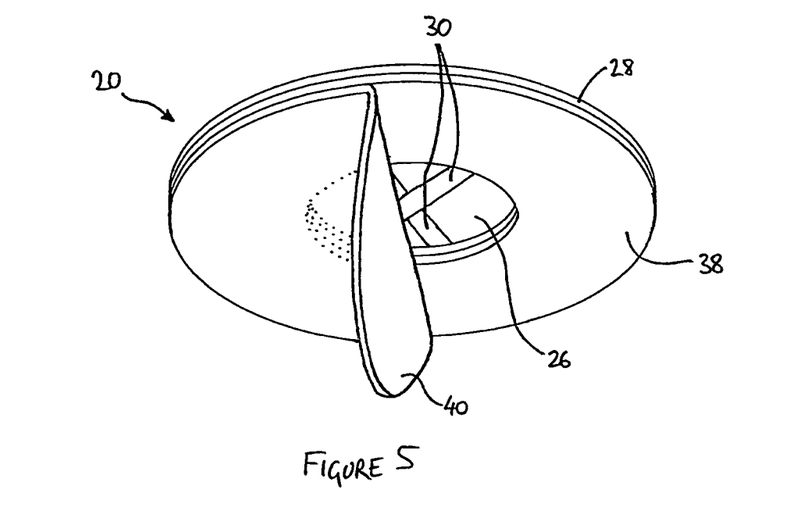
FIG. 5 is a perspective drawing showing the underside of the transducer holder of FIG. 2.

As shown most clearly in FIG. 5, the bottom surface of the ring 28 is provided with an adhesive layer 38 which may be coated or otherwise applied to the ring 28. The adhesive layer is itself annular, substantially of the same size as the ring 28.

The adhesive material of the adhesive layer 38 is of a known type suitable for effecting a strong but non-permanent bond with the patient's skin. For example, a suitable adhesive is hydrocolloid adhesive supplied by Coloplast Ltd.

The transducer holder 20 is provided with a removable backing layer 40 shown partially removed in FIG. 5, which covers the adhesive layer 38 to prevent the adhesive drying out or sticking to anything else before use, such as to packaging during storage. A tab (not shown) may project beyond the general periphery of the backing layer 40 to ease its removal.

When required for use on a patient, the backing layer 40 is peeled off the adhesive layer 38 and the transducer holder 20 is applied to the patient's skin 12 in the desired location. The adhesive layer 38 adheres to the skin 12 and keeps the holder 20 in position on the patient. The transducer 36 is then inserted through an insertion opening 34, so that its face is pressed through the aperture 26 against the patient's abdomen. As the bands 30 must deform elastically in order to accommodate the transducer 36, the elastic restoring forces of the bands 30 provide a net force acting on the transducer 36 in the direction of the patient's abdomen. This net force pushes the face of the transducer 36 against the patient's abdomen to maintain acoustic contact. By a combination of the adhesive layer 38 and the elastic retainer 24 defined by the bands 30, the transducer 36 is held firmly in place against the patient's body, even if the patient moves or rolls over.

Figure 6:
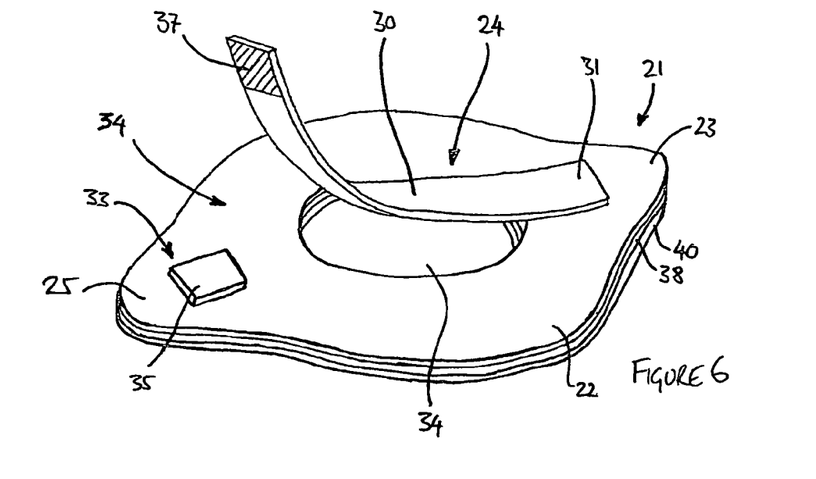
FIG. 6 is a perspective drawing of a transducer holder according to a second embodiment of the present invention.
Figure 7:
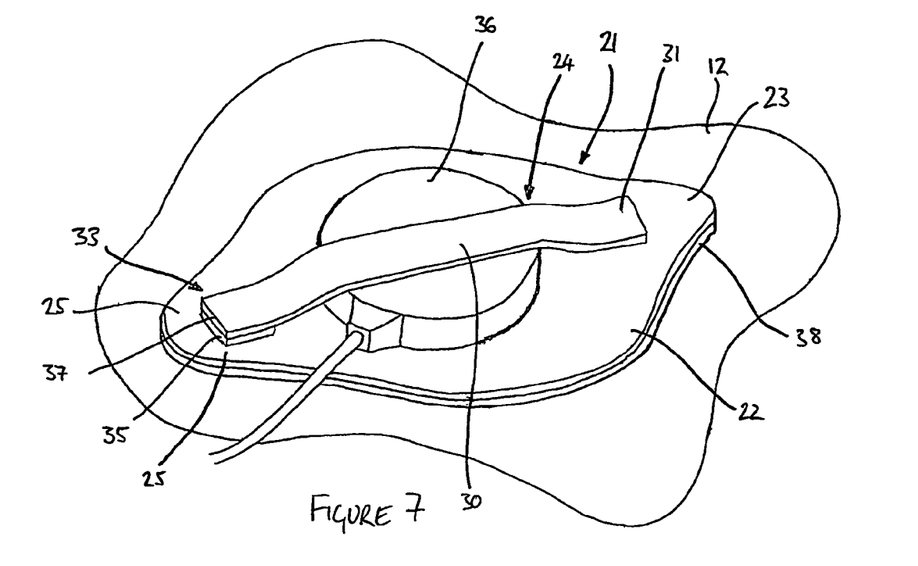
FIG. 7 is a perspective drawing of the transducer holder of FIG. 6, in use holding a transducer in a desired position on a patient's abdomen.

In describing a second embodiment of the present invention, the transducer holder 21 shown in FIGS. 6 and 7, like numerals will be used for like parts. In this embodiment, the base 22 is provided with a first extended anchor portion or wing 23 and a second extended anchor portion or wing 25. The wings 23, 25 of the base 22 are disposed diametrically opposite one another with respect to the opening 34, so that the opening 34 is located between the wings 23, 25.

The retainer 24 comprises a band 30. The band 30 is attached to the base 22 at a first attachment point 31 and is attachable to the base 22 at a second attachment point 33. The first attachment point 31 is located adjacent to the first wing 23 of the base 22, so that the first attachment point 31 is inboard of the first wing 23 of the base. At the second attachment point 33, there is provided a releasable hook-and-loop fastening comprising a loop pad 35 and a complementary hook pad 37. The loop pad 35 is located adjacent to the second wing 25 of the base 22, so that the loop pad 35 is located inboard of the second wing 25 of the base. The hook pad 37 is located on the underside of the band 30, as can be seen in FIG. 6 in which the band 30 is shown detached from the base 22 at the second attachment point 33.

When the band 30 is detached from the base 22 at the second attachment point 33, the band can move to accommodate a transducer 36. In this way, an insertion opening 34, through which the transducer can pass, is defined when the band 30 is detached from the base 22 at the second attachment point 33. It is also possible to use the releasable attachment facility to impart a desired tension to the band to determine the retention force applied by the band to a transducer. The band may already be attached at both ends to the base before the transducer is inserted through the insertion opening.

In use, the transducer holder 21 is attached to the skin 12 of a patient by way of an adhesive layer 38 as in the first embodiment of the invention. The transducer 36 is inserted into the holder 21 by way of the insertion opening 34 formed when the band 30 is detached from the base 22 at the second attachment point 33. The hook pad 37 is applied to the loop pad 35 so as to attach the band 30 to the base 22 at the second attachment point 33, as shown in FIG. 7.

When the band 30 is attached to the base 22 at the second attachment point 33, the band is pulled tightly across the transducer 36 to provide a net force acting on the transducer 36 in the direction of the patient's abdomen. This net force pushes the face of the transducer 36 against the patient's abdomen to maintain acoustic contact. By a combination of the adhesive layer 38 and the retainer 24 defined by the band 30, the transducer 36 is held firmly in place against the patient's body, even if the patient moves or rolls over.

In use, the band 30 pulls the attachment points 31, 33 towards one another, so that the base 22 has a tendency to peel away from the skin 12. To prevent peeling of the base 22 from the skin 12, the adhesive bond between the base 22 and the skin 12, effected by the adhesive layer 38, must be stronger than the peeling force acting on the base 22 at the attachment points 31, 33.

In this embodiment, the attachment points 31, 33 are located adjacent to the wings 23, 25 of the base 22, so that the area of the base 22 in adhesive contact with the skin 12, via the adhesive layer 38, is relatively large in the vicinity of the attachment points 31, 33. As a result, the adhesive bond between the base 22 and the skin 12 is enhanced in the vicinity of the attachment points 31, 33 due to the presence of the wings 23, 25 so as to prevent the base 22 peeling from the skin 12. Furthermore, because the attachment points 31, 33 are located inboard of the wings 23, 25 of the base 22, a peeling force does not arise at the edge of the base 22. Alternatively, the attachment points 31, 33 may be located on the wings 23, 25 of the base.

Figure 8:
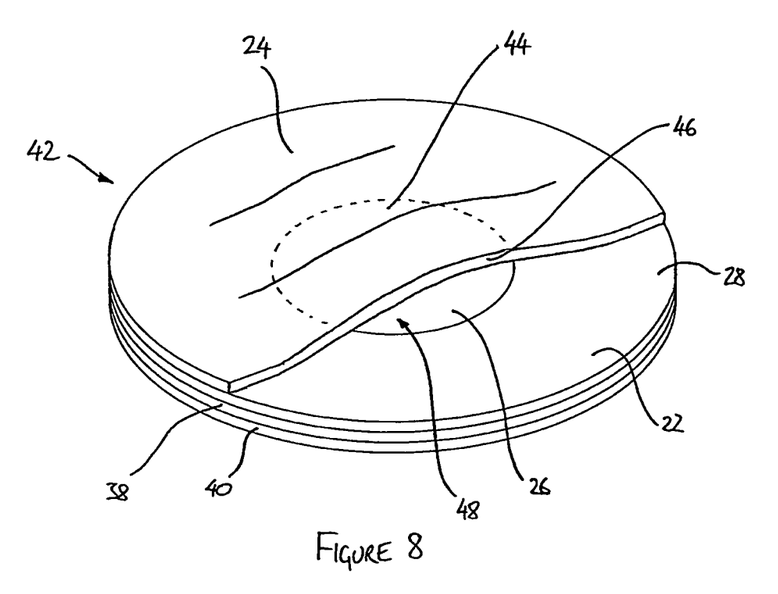
FIG. 8 is a perspective drawing of a transducer holder according to a third embodiment of the present invention.

In describing a third embodiment of the present invention, the transducer holder 42 shown in FIG. 8, like numerals will be used for like parts. In this embodiment, the elastic retainer 24 is a resiliently-stretchable polymeric membrane 44. The provision of a membrane 44 is advantageous in that it covers the transducer in use and so protects the transducer from soiling.

The membrane 44 is attached to the ring 28 around most of its periphery and is part-circular, terminating in an unattached free edge 46 that is a chord of the circle. In plan view, the free edge 46 is disposed slightly outside the aperture 26 in the ring 28. Otherwise, the membrane 44 is of substantially the same diameter as the ring 28, or at least wider than the aperture 26 so as to provide for attachment to the ring 28.

It will be appreciated that the membrane 44 and the base 22 therefore define a pocket that receives a transducer in use. The transducer is introduced through an insertion opening 48 defined between the free edge 46 of the membrane 44 and the ring 28. Like the bands 30 of the first embodiment, the membrane 44 defines a shallow hump in cross-section to ease insertion of the transducer. The membrane 44 is therefore slightly wider in its unattached state than when attached to the ring 28.

The dimensions of the membrane 44 and the insertion opening 48 are such that the membrane 44 must deform elastically to accommodate a transducer within the space between the membrane 44 and the base 22. The elastic restoring forces exerted by the membrane 44 cause a net force to act on the transducer, pushing it against the patient's abdomen through the aperture 26 of the base 22. The restoring forces also retain the transducer within the holder 42 under the normal conditions of use, for example when the patient moves. However, the transducer can be removed from the holder 42 through the insertion opening 48 when required, simply by pulling out the transducer against the resilience of the membrane 44.

Figure 9:
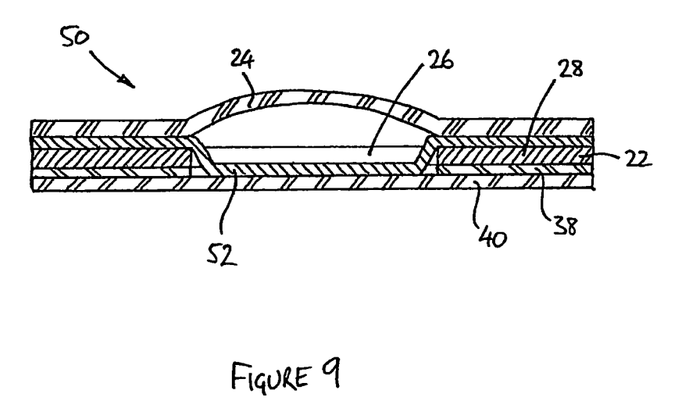
FIG. 9 is a sectional drawing of a fourth embodiment of the present invention.

In a fourth embodiment of the present invention, shown in FIG. 9, a transducer holder 50 that is otherwise similar to the first, second and third embodiments further comprises a barrier film 52 which extends across the aperture 26 of the base 22. The barrier film 52 is attached to the top surface of the ring 28 and, as illustrated, is dished by the thickness of the ring 28 to lie against the patient's skin when the backing layer 40 has been peeled off and the adhesive layer 38 has been applied to the skin. The barrier film 52 is advantageous in that it prevents direct contact between the transducer and the patient and therefore helps to keep the transducer clean. It also reduces the risk to the patient of cross-infection from a soiled transducer.

Acoustic contact between the face of the transducer and the patient's skin is maintained through the barrier film by the action of the elastic restoring forces of the retainer acting on the transducer as previously described.

Figure 10:
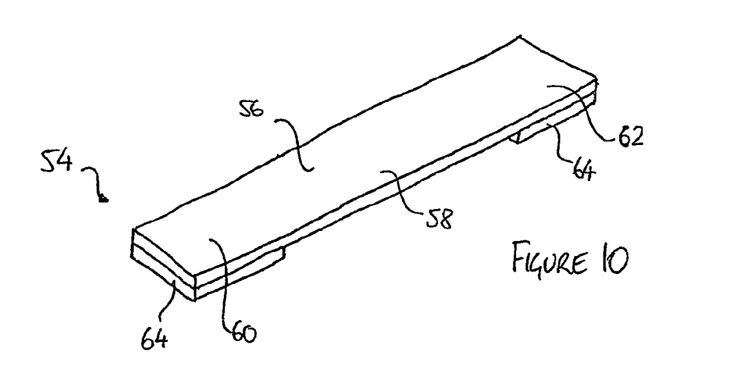
FIG. 10 is a perspective drawing of a transducer holder according to a fifth embodiment of the present invention.
Figure 11:
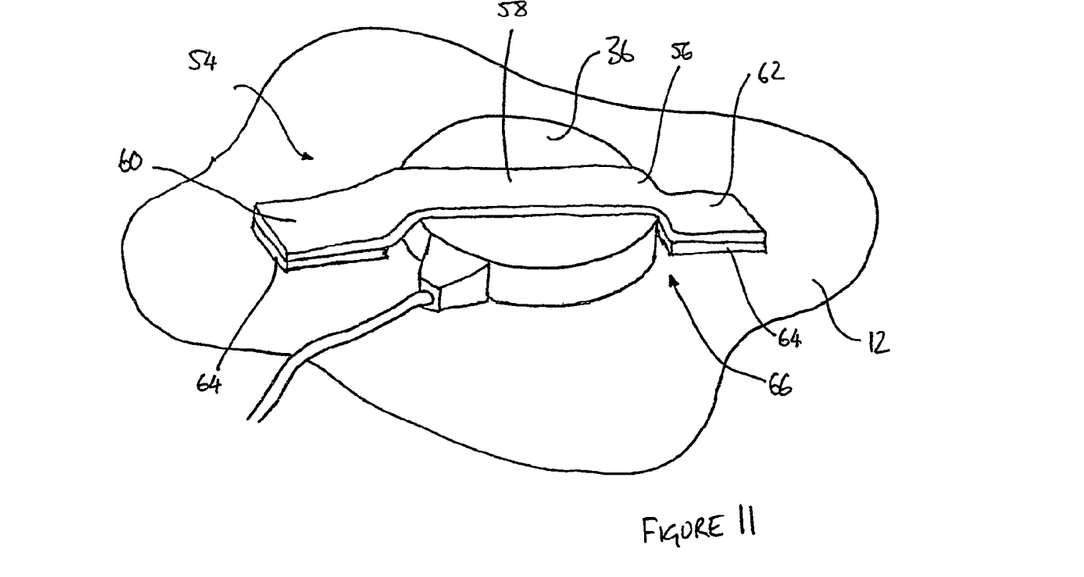
FIG. 11 is a perspective drawing of the transducer holder of FIG. 10, in use holding a transducer in a desired position on a patient's abdomen.

In a fifth embodiment of the present invention, shown in FIGS. 10 and 11, a transducer holder 54 is provided which comprises a single generally elongate band or strip 56 of flexible material. A central portion 58 of the strip 56 defines a retainer of the transducer holder 54, and end portions 60, 62 of the strip 56 together define a base of the transducer holder 54.

The strip 56 carries an adhesive layer 64 for releasably attaching the strip 56 to the patient's skin 12. The adhesive layer 64 extends across the end portions 60, 62 of the strip 56, but is absent from the central portion 58 of the strip 56. At least the central portion 58 of the strip 56 is elastically extensible.

In use, the holder 54 is applied to the patient's skin 12 so that both the end portions 60, 62 and the central portion 58 of the strip lie against the patient's skin 12. The adhesive layer 64 on each end portion 60, 62 adheres to the skin 12 and keeps the holder 54 in position on the patient. The transducer 36 is then inserted between the central portion 58 of the strip 56 and the skin 12 of the patient, so that the face of the transducer 36 is pressed against the patient's abdomen. In this way, the central portion 58 of the strip 56 partially defines an insertion opening 66 for the transducer 36, and the gap between the adhesive end portions 60, 62 of the strip 56 defines an aperture of the base through which the face of the transducer 36 is presented to the skin 12.

As the central portion 58 of the strip 56 must deform elastically in order to accommodate the transducer 36, the elastic restoring forces of the central portion 58 of the strip 56 provide a net force acting on the transducer 36 in the direction of the patient's abdomen. This net force pushes the face of the transducer 36 against the patient's abdomen to maintain acoustic contact. The length and elastic properties of the central portion 58 of the strip 56 are such that the magnitude of the restoring force is optimised to provide good acoustic contact while avoiding discomfort of the patient.

It will be appreciated that the transducer holder 54 of the fifth embodiment could be provided with a removable backing layer (not shown) to cover the adhesive layer 64 as in the previous embodiments of the invention. The adhesive layer may extend across the central portion 58 of the strip 56, in which case a covering layer (not shown) may be carried on the adhesive layer on the central portion of the strip so as to prevent the strip sticking to the transducer, in use. A barrier layer (not shown), extending between the end portions 60, 62 of the strip 56 so as to lie underneath the transducer 36, in use, may also be provided as previously described.

If desired, in any embodiment of the invention, acoustic contact can be further improved by applying a layer of acoustic gel between the transducer and the skin or between the transducer and the barrier film, if present. For example the transducer holder may be supplied with the upper surface of the barrier film pre-coated with acoustic gel. Moreover, acoustic gel may also be applied between the barrier film, if present, and the skin.

Because the transducer holder of the invention is simple in construction and can be easily manufactured from cheap materials, it can be produced at low cost and is suitable for disposable, once-only use.

It will be apparent to the reader that several modifications are possible within the scope of the present invention. For example, when an aperture in the base is provided, the aperture may be larger than, smaller than, or the same diameter as, the face of the transducer. Also, as some transducers have more than one sensor or transmitter on their face, it is possible to provide more than one aperture in the base.

It will be appreciated that the retainer could comprise any arrangement appropriate for providing the necessary force on the transducer. If the retainer comprises bands in accordance with the first or second embodiments of the invention, or strips in accordance with the fifth embodiment of the invention, any number of bands or strips in any geometrical arrangement could be provided.

In the first embodiment of the invention, for example, a single wide band could be provided, delivering two insertion openings, one to each side of the band. Two or more bands could be arranged parallel to one another as chords, defining insertion openings between the bands and/or outside the bands. Alternatively, more than two bands could be disposed across diameters of the base at suitable mutual orientations, for example at equiangular intervals. It is also possible for two or more bands to be oriented other than in equi-angular disposition. A combination of diametric and other chordal bands could also be provided. Similar geometric arrangements of bands are possible in accordance with the second embodiment of the invention. More than one band may be provided, and the or each band may be releasably attachable to the base at one or both ends. For example, a single band may be provided which is releasably attachable to the base at both ends of the band, so that the band can be removed completely from the base for insertion of the transducer holder. In another example, two bands are arranged orthogonally to one another, each band passing diametrically across the opening and each having a releasable attachment at one end or both ends.

In the fifth embodiment of the invention, one or more strips can be arranged in the same manner as the band or bands described above.

The insertion opening could be provided in any convenient way. For example, in the third embodiment of the invention, the insertion opening could be a slit or hole in the membrane, in which case the membrane could be completely circular such that the entire perimeter of the membrane could be attached to the base. Also, the transducer could be introduced to the transducer holder through the aperture in the base, in which case the insertion opening could be designed to allow passage of the connecting lead, if present.

If the retainer is a membrane, part or all of the membrane may be releasably attachable to the base. For example, a majority of the perimeter of the membrane could be attached to the base, while a minority of the perimeter of the membrane could be releasably attachable to the base to provide an insertion opening when detached from the base.

The transducer holder of any embodiment may be arranged to accommodate a transducer having a stud, such as the transducer shown in FIG. 1. For example, a slit may be provided in a retainer comprising a strip, a band or a membrane, and the stud of the transducer may be inserted through the slit, in use. In another possible arrangement, the retainer comprises two or more bands, and the bands are arranged so that the stud of the transducer is held between two of the bands, in use.

In embodiments of the invention where the retainer is releasably attachable to the base, any suitable means of releasable attachment may be employed. For example, instead of a hook-and-loop fastening, a press-stud fastening or a releasable adhesive may be employed. A releasable attachment means may be provided in combination with an elastic retainer such as one or more elastic bands or an elastic membrane, or alternatively the retainer may not be appreciably elastic.

Advantageously, the adhesive of the adhesive layer can be re-adhered to the skin after removal, so that the transducer holder can be removed and re-applied as necessary. Other adherent arrangements are possible within the broadest concepts of the invention. For example, the adhesive layer and backing layer may be omitted and an alternative means of affixing the transducer holder to the patient's skin may be provided, for example double-sided tape or a separately applied adhesive. Furthermore, the transducer holder could be attached to the patient's skin by suction, for example by shaping the base to act as a suction cup.

Alternative embodiments of the barrier film lie within the scope of the present invention. For example, the barrier film may be attached to the bottom surface of the ring. Alternatively, a barrier between the patient and the transducer may be provided by eliminating the aperture of the base so that the material of the base itself forms the barrier. That is to say, the base can be a simple acoustically-transparent disc rather than being defined by a ring around an aperture. Moreover, the adhesive layer may or may not extend across all or part of the underside of the barrier film.

Conveniently, a plurality of transducer holders may be stored in a suitable dispenser to allow a practitioner to easily obtain a transducer holder when required for use. It will be appreciated that several dispenser arrangements are possible. For example, a stack of transducer holders may be provided in a box, the box having an aperture in one face of the box through which individual transducer holders can be removed when required for use. The stack of holders may be arranged within the box so that only the next available transducer holder need be touched by the practitioner when selecting a holder, thus avoiding unnecessary contact with the remaining holders and reducing the risk of cross-infection. The aperture may be provided in an upper face of the box, so that the box could be placed on a work surface, or in a side or bottom face of the box so that the box could be wall-mounted. The dispenser may be arranged so that the action of removing one holder from the box moves the next holder to be removed into an accessible position. A disposable box could be provided along with the transducer holders, or a refillable box could be provided for replenishment with transducer holders when necessary.

In a further example, a plurality of transducer holders may be provided in a roll-type dispenser. Elegantly, transducer holders could be provided on a roll of backing paper, so that the backing paper acts as the backing layer of each transducer holder. The roll could be provided in a dispenser box having an aperture to allow an end of the roll to protrude from the box. In this way, a transducer holder can be prepared for use by pulling the end of the roll to give access to a transducer holder, then peeling the holder from the backing paper so as to expose the adhesive layer. Again, only the next available holder is accessible at any time, so that the risk of cross-contamination is minimized.

The transducer holder could be of any size and shape appropriate for accommodating any design of transducer. Therefore, whilst having particular advantages in the field of obstetrics, the present invention is not limited to any specific design of transducer, and could be used in many different medical procedures.

For these and other reasons, reference should be made to the accompanying claims rather than to the foregoing specific description in interpreting the scope of the invention.

The invention claimed is:

1. A transducer holder for holding a transducer in signal-receiving contact with a patient's body, the holder comprising:
 a base adherently attachable to the patient's skin; and
 a retainer attached or attachable to the base;
 wherein, in use, the retainer holds the transducer in signal-receiving contact with the patient's body and retains the transducer in the holder; and
 wherein the retainer is an elastically deformable membrane or one or more bands which, in use, extends over the transducer held by the holder and deforms elastically to accommodate the transducer, such that elastic restoring forces exerted by the retainer retain the transducer within the holder, and cause a net force to act on the transducer pushing it against the patient's skin;
 wherein the transducer holder comprises an elongate strip of flexible material that includes an elastically extensible central portion that defines the retainer, and two or more end portions that together at least partially define the base; and
 wherein, when the base is adherently attached to the patient's skin, the retainer partially defines the insertion opening for the transducer and the end portions define an aperture of the base through which the transducer is presented to the patient's skin.

2. The transducer holder of claim 1, wherein the base is a flexible disc adhesively attachable to the patient's skin and adapted to permit said signal-receiving contact through the base.

3. The transducer holder of claim 2, wherein the retainer comprises one or more bands that, in use, extend over the transducer held by the holder.

4. The transducer holder of claim 2, wherein the retainer comprises a membrane that, in use, extends over the transducer held by the holder and wherein the membrane is attached or attachable to the base around a major portion of its periphery, a minor unattached peripheral portion of the membrane having a free edge.

5. The transducer holder of claim 4, wherein the base has an aperture for enabling said signal-receiving contact.

6. The transducer holder of claim 5, further comprising a barrier film through which signal-receiving contact is effected, the barrier film extending across the aperture.

7. The transducer holder of claim 1, wherein the base comprises two or more portions, each portion being attachable to the patient's skin.

8. The transducer holder of claim 2, wherein the base has at least one enlarged anchor region, and the retainer is attached or attachable to the base at or adjacent to each anchor region.

9. The transducer holder of claim 2, wherein the retainer is elongate and comprises a first end and a second end, and wherein at least one of the ends is releasably attached to the base.

10. The transducer holder of claim 2, wherein the retainer comprises one or more bands that, in use, extend over the transducer held by the holder and wherein at least one of the bands defines the periphery of the insertion opening.

11. The transducer holder of claim 10, wherein the retainer comprises a membrane having free edges, and wherein the free edges of the membrane define the periphery of the insertion opening.

12. The transducer holder of claim 2, wherein the base defines the insertion opening.

13. The transducer holder of claim 2, wherein the insertion opening is defined by the combination of the retainer and the base.

14. The transducer holder of claim 13, wherein the retainer comprises one or more bands that, in use, extend over the transducer held by the holder and wherein one of said bands defines a portion of the periphery of the insertion opening.

15. The transducer holder of claim 13, wherein the retainer comprises a membrane having a free edge, and wherein the free edge of the membrane defines a portion of the periphery of the insertion opening.

16. The transducer holder of claim 3, wherein at least one of the one or more bands is releasably attached to the base.

17. The transducer holder of claim 3, wherein the retainer comprises two or more bands that intersect with one another.

18. A transducer holder for holding a transducer in signal-receiving contact with a patient's body, the holder comprising:
- an adhesive layer having a removable backing layer on one side of the adhesive layer;
- a flexible disc having a disc opening such that the flexible disc is an annular ring, said annular ring adhesively attached to the side of the adhesive layer opposite that of the backing layer, wherein said disc opening is sized to snugly receive the transducer; and
- an elastic retainer configured to retain the transducer in signal-receiving contact with the patient's skin;
- wherein the adhesive layer comprises an opening sized to snugly receive the transducer, said adhesive layer opening is oriented in alignment with the disc opening such that the disc opening and the adhesive layer opening together form a transducer-receiving opening
- wherein the transducer holder comprises an elongate strip of flexible material that includes an elastically extensible central portion that defines the retainer, and two or more end portions that together at least partially define the annular ring; and
- wherein, when the annular ring is adherently attached to the patient's skin, the retainer partially defines the insertion opening for the transducer and the end portions define an aperture of the annular ring through which the transducer is presented to the patient's skin.

19. The transducer holder of claim 18, wherein the elastic retainer comprises two elastic bands configured in a crossing orientation, each of said elastic bands attached to the annular ring by an attachment point at each end of the band, the elastic bands configured to deform elastically to admit the transducer into the transducer-receiving opening, and then to elastically contract to retain the transducer in signal-receiving contact with the patient's body.

20. The transducer holder of claim 19, wherein the flexible disc and the adhesive layer further comprise a plurality of wings, each of said wings being an anchor point for attachment of an end of an elastic band.

21. The transducer holder of claim 18, wherein the elastic retainer comprises a resiliently-stretchable, polymeric, circular segment membrane attached to the annular ring along the arc of the circular segment membrane and terminating at the free edge defined by the chord of the circular segment membrane.

\* \* \* \* \*